(12) United States Patent
Ryan

(10) Patent No.: US 10,675,179 B2
(45) Date of Patent: Jun. 9, 2020

(54) CANNULA TOOL AND METHOD

(71) Applicant: Edwin Ryan, St. Paul, MN (US)

(72) Inventor: Edwin Ryan, St. Paul, MN (US)

( * ) Notice: Subject to any disclaimer, the term of this patent is extended or adjusted under 35 U.S.C. 154(b) by 99 days.

(21) Appl. No.: 15/109,391

(22) PCT Filed: Dec. 19, 2014

(86) PCT No.: PCT/US2014/071681
§ 371 (c)(1),
(2) Date: Jun. 30, 2016

(87) PCT Pub. No.: WO2015/102965
PCT Pub. Date: Jul. 9, 2015

(65) Prior Publication Data
US 2016/0317351 A1 Nov. 3, 2016

Related U.S. Application Data

(60) Provisional application No. 61/921,980, filed on Dec. 30, 2013.

(51) Int. Cl.
*A61F 9/007* (2006.01)
*A61M 5/158* (2006.01)
*A61B 17/00* (2006.01)
*A61B 17/04* (2006.01)

(52) U.S. Cl.
CPC .......... *A61F 9/007* (2013.01); *A61F 9/00709* (2013.01); *A61F 9/00736* (2013.01); *A61B 17/0482* (2013.01); *A61B 2017/00907* (2013.01); *A61M 5/158* (2013.01);
(Continued)

(58) Field of Classification Search
CPC .. A61F 9/007; A61F 9/00709; A61F 9/00736; A61F 9/00781; A61B 17/0482; A61B 17/28; A61B 17/30; A61M 2005/1583
See application file for complete search history.

(56) References Cited

U.S. PATENT DOCUMENTS

| 4,494,543 A * | 1/1985 | Hart ................... A61B 17/30 606/133 |
| 7,682,372 B2 * | 3/2010 | Peterson ............ A61B 17/04 606/211 |
| 7,846,134 B1 | 12/2010 | Nadolski et al. |

(Continued)

FOREIGN PATENT DOCUMENTS

| WO | WO-2015102965 A2 | 7/2015 |
| WO | WO-2015102965 A3 | 7/2015 |

OTHER PUBLICATIONS

International Application Serial No. PCT/US2014/071681, International Search Report dated Apr. 20, 2015, 2 pgs.
(Continued)

*Primary Examiner* — Sarah W Aleman
(74) *Attorney, Agent, or Firm* — Schwegman Lundberg & Woessner, P.A.

(57) ABSTRACT

An ophthalmic tool and methods are shown. Examples of ophthalmic tools include cannula removal portions that include one or more grippers. In use the grippers, a mandrel, and a tool base provide a surgeon with a level of control that facilitates removal of a cannula. Other examples include a wound visualization tool that may be in combination with a cannula remover.

15 Claims, 5 Drawing Sheets

(52) U.S. Cl.
CPC .............. *A61M 2005/1583* (2013.01); *A61M 2005/1588* (2013.01)

(56) References Cited

U.S. PATENT DOCUMENTS

| | | | |
|---|---|---|---|
| 2004/0073231 A1* | 4/2004 | Juan, Jr. .................. | A61F 9/007 606/108 |
| 2007/0187440 A1* | 8/2007 | Rosenbaum ......... | A47G 25/901 223/111 |
| 2007/0213767 A1 | 9/2007 | Ravikumar | |
| 2008/0033462 A1* | 2/2008 | Di Nardo ................ | A61F 9/007 606/166 |
| 2011/0046712 A1 | 2/2011 | Melsheimer et al. | |
| 2011/0213386 A1* | 9/2011 | Ryan ..................... | A61B 17/04 606/148 |
| 2011/0288525 A1* | 11/2011 | Hallen ............... | A61B 17/0057 604/506 |

OTHER PUBLICATIONS

International Application Serial No. PCT/US2014/071681, Written Opinion dated Apr. 20, 2015, 6 pgs.

* cited by examiner

CANNULA TOOL AND METHOD

CLAIM OF PRIORITY

This application is a U.S. National Stage Filing under 35 U.S.C. 371 from International Application No. PCT/US2015/071681, filed on Dec. 19, 2014, and published as WO 2015/102965 A2 on Jul. 9, 2015, which claims the benefit of priority under 35 U.S.C. § 119(e) to U.S. Provisional Patent Application Ser. No. 61/921,980, filed on Dec. 30, 2013, each of which is hereby incorporated by reference herein in its entirety.

TECHNICAL FIELD

This invention relates to devices and methods for phthalmological procedures, such as an infusion procedure.

BACKGROUND

A number of ophthalmological procedures require insertion of a cannula. One example includes use of a cannula with an infusion line. After a procedure is completed, the cannula must be removed. It is desirable to provide a tool for safe and easy removal of a cannula. It is also desirable to provide tools that are useful for completing other portions of an ophthalmological procedure.

DETAILED DESCRIPTION

Figure 1:
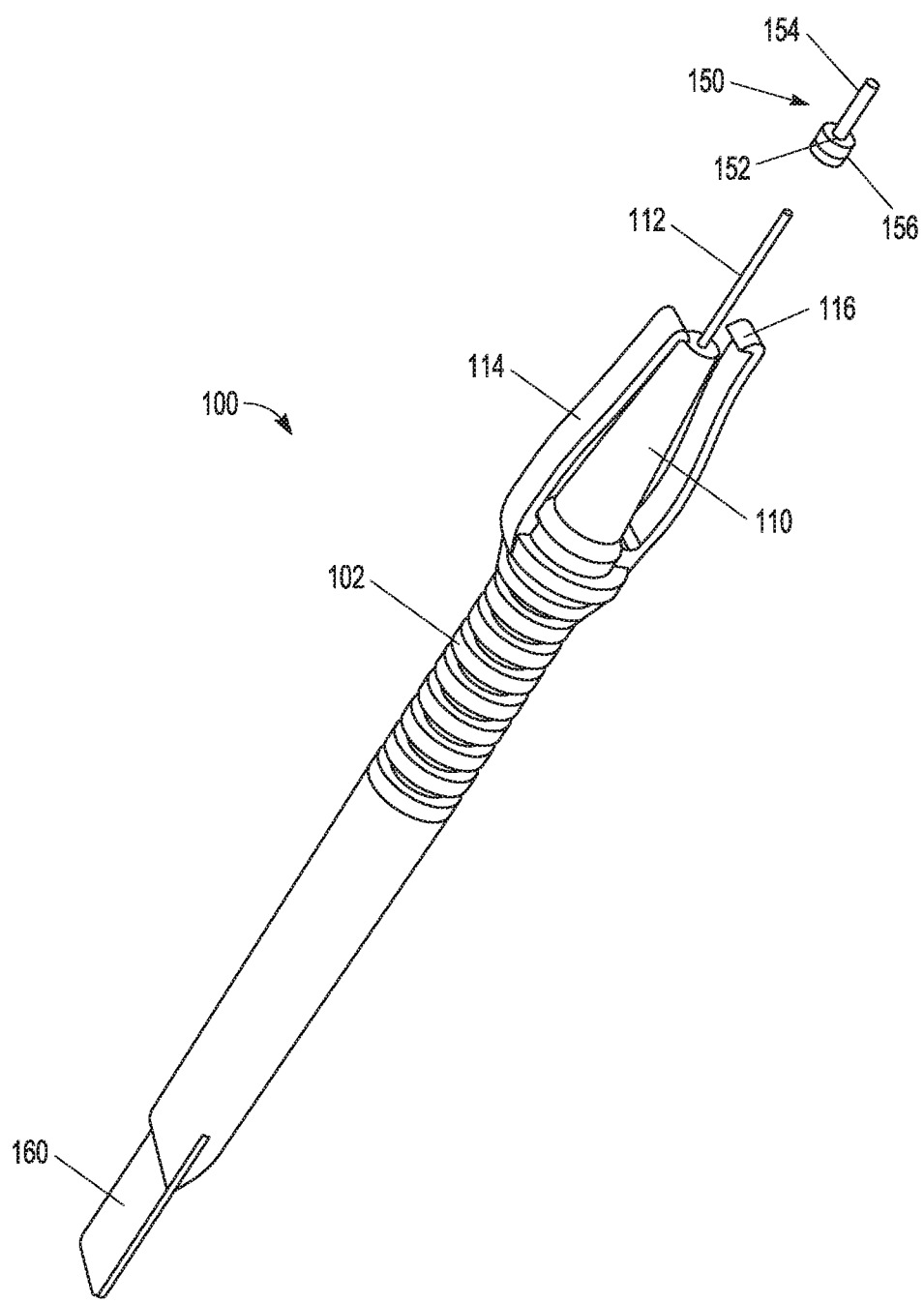
FIG. 1 shows a cannula tool according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an ophthalmic tool 100 according to one example of the invention. The ophthalmic tool 100 includes a handle 102 that connects to a tool base 110. The tool base 110 is sized to accept a cannula 150. In the example shown, a base 152 of the cannula 150 has a diameter that is approximately the same as a diameter of the tool base 110. In use, the base 152 of the cannula 150 abuts the tool base 110 and the contact between the base 152 of the cannula 150 and the tool base 110 provides a surgeon with a level of control over an orientation of the cannula 150 as it is removed from a patient's eye.

The ophthalmic tool 100 further shows a mandrel 112 extending from the tool base 110. In one example of use, the mandrel 112 is inserted through the base 152 and into a tube 154 of the cannula 150 until the base 152 abuts the tool base 110. Contact between the base 152 of the cannula 150 and the tool base 110, along with the mandrel provide an increased level of control over an orientation of the cannula 150 as it is removed from a patient's eye.

The ophthalmic tool 100 further shows grippers 114 extending around the tool base from the handle. In the example of FIG. 1, two grippers 114 are shown, although the invention is not so limited. Other numbers of grippers, such as one, three, four, or more than four grippers 114 may also be used. In the example of FIG. 1, the pair of grippers 114 are opposing one another, facilitating a squeezing or pinching of the grippers 114 to engage the cannula 150 for a removal operation.

In the example of FIG. 1, the grippers 114 include a hooked end 116. In one example, the hooked end 116 is adapted to engage a ridge 156 on the base 152 of the cannula 150 when in use.

Figure 2:
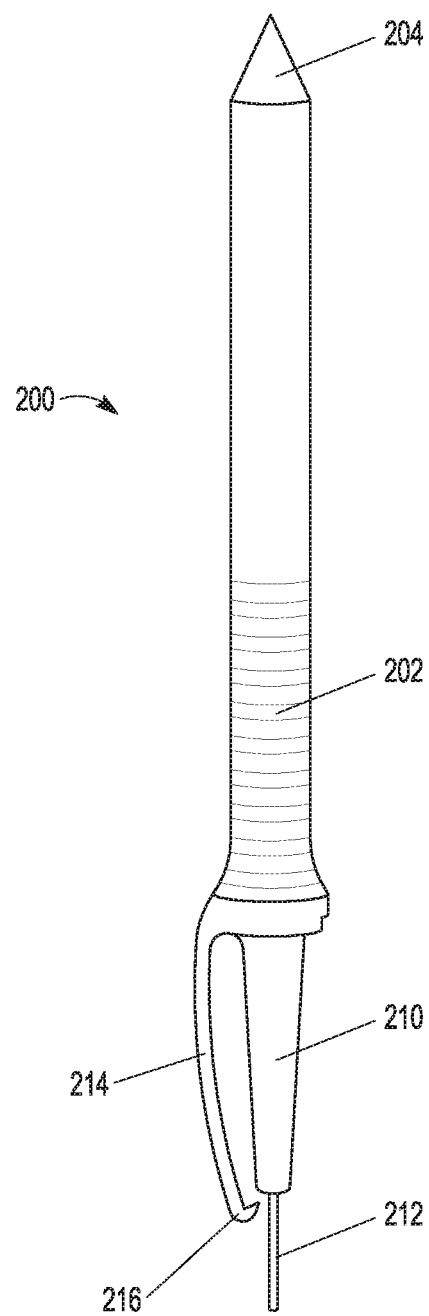
FIG. 2 shows a portion of a cannula tool according to an embodiment of the invention.

Another configuration is shown in FIG. 2. FIG. 2 shows an ophthalmic tool 200 including a handle 202 similar to the ophthalmic tool 200 from FIG. 1. The ophthalmic tool 200 includes a mandrel 212, and a single gripper 214. In one example, using the ophthalmic tool 200 of FIG. 2, the gripper 214 may engage the cannula 150, for example using the ridge 156. In one example a single gripper 214 is useful, for re-insertion of a cannula that may have become dislodged from a patient's eye during a procedure. The single gripper 214 engages the cannula 150 by pressing the base 152 between the single gripper 214 and the mandrel 212. By angling the ophthalmic tool 200 into position with the single gripper 214 positioned away from a surface of the patient's eye, the cannula 150 may be pushed back into place against the patient's eye. Because only one gripper 214 is present, the gripper 214 need not get in the way, and the cannula 150 may be placed closer to the patient's eye.

In one example, a number of portions of the ophthalmic tool (100, 200) may be integrally molded. In one example, portions of the ophthalmic tool (100, 200) are formed from a polymeric material. Any suitable polymer that provides the desired properties, such as flexibility for the grippers, may be used. It is desirable to use materials that are biocompatible. Other example materials may include metal, such as titanium or stainless steel, etc.

In one example, the handle 102, tool base 110, and grippers 114 are integrally formed. These components may be integrally formed, for example, by injection molding. In other examples, different materials may be used to manufacture different components, and the ophthalmic tool 100 may be assembled from multiple parts. One advantage of integral forming includes ease of forming and reduced manufacturing cost.

In another example, as shown in FIG. 1, the ophthalmic tool 100 includes a visualization tool 160. In one example the visualization tool 160 includes a substantially transparent portion to place in contact with an eye near an ophthalmic wound. After a cannula 150 is removed the remaining wound may require a suture to close the wound. As described below, in some examples, it may be difficult to see the wound and as a result, difficult to suture the wound, if needed. FIG. 2 also shows a location 204 for a visualization tool similar to visualization tool 160.

Figure 3:
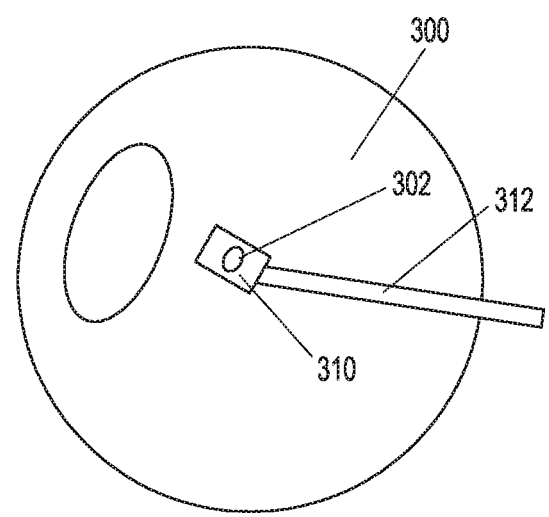
FIG. 3 shows a visualization device according to an embodiment of the invention.

FIG. 3 shows a visualization tool that is used to view a wound 302, and can be used for visualization only, or used in conjunction with a suturing operation. The Figure illustrates a glass or plastic transparent portion 310 and a handle 312. In one example, a handle as described in embodiments above in FIGS. 1-2 is used. It can often be difficult to visualize a small wound 302 due to fluids or blood present in the area, and the wound 302 itself being normally closed without any external pressure.

Using the visualization tool, pressure is put on the eye 300 in the general area of the wound 302. The pressure causes the fluids and/or blood to move away from the wound 302, and makes the wound 302 easier to visualize. Once the wound is located, the surgeon can proceed with suturing.

Figure 4:
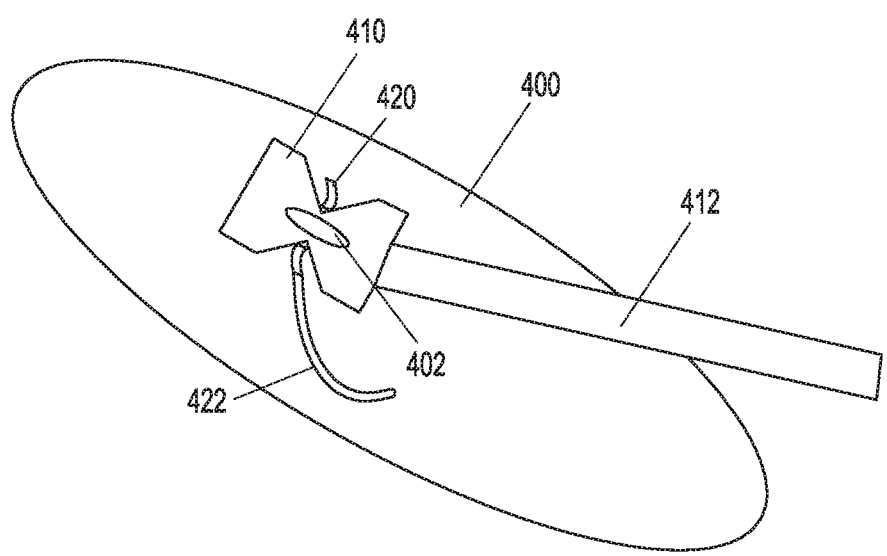
FIG. 4 shows another visualization device according to an embodiment of the invention.

FIG. 4 illustrates another example of a visualization tool that may be used for viewing an ophthalmic wound and/or used to suture an ophthalmic wound. A transparent portion 410 is shaped thinner in the middle, for example as an hourglass shape. The wound 402 in the eye 400 is still visible as described in FIG. 5 above. However, due to the thinner middle of the transparent portion 410, a suture 420 can easily be inserted to close the wound 402 without having to remove the transparent portion 410. A needle 422 is shown pulling in the modified suture 420. An optional handle 412 is shown to better hold the transparent portion 410 and to put pressure on the eye 400.

Figure 5:
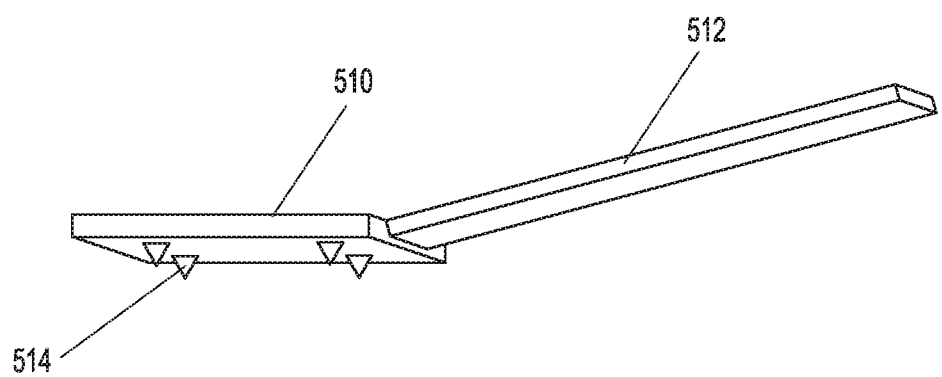
FIG. 5 shows another visualization device according to an embodiment of the invention.

FIG. 5 shows another example of a visualization tool that may be used for viewing an ophthalmic wound and/or used to suture an ophthalmic wound. A transparent portion 510 is shown with an optional handle 512. Although an elongated handle 512 is illustrated, any number of handle configurations are within the scope of the invention. In one example, a handle as described in embodiments above in FIGS. 1-2 is used. A rectangular shape of the transparent portion 510 is shown, however shapes such as an hourglass shape described above, or other shapes are within the scope of the invention.

A number of teeth 514 or other frictional protrusions are shown on surface of the transparent portion 510 that is to be adjacent to the eye. By using teeth 514, a surgeon may grip the sclera of the eye with one hand to prevent rotation of the eye and aid in visualizing the wound simultaneously while the sutures are being placed with the other hand. The ability to grip the sclera may be particularly useful in for suturing due to torque that may be placed on the eye during suturing. In one example, a frictional protrusion, similar to the teeth 514 of FIG. 5 are incorporated into the handle 102 of the ophthalmic tool 100 of FIG. 1, or the ophthalmic tool 200 of FIG. 2, and located adjacent to the visualization tool 160 or at the location 204 for a visualization tool similar to visualization tool 160.

In one example, it is useful to have both a cannula tool as described in embodiments above, and a visualization tool as described in embodiments above on the same handle. As noted above, one source of a wound that may benefit from a visualization tool includes a wound from insertion of a cannula. Once the cannula is removed, the next logical step is to visualize and suture the wound. It is beneficial to a surgeon to not have to find an additional tool when performing such a procedure. As described above, the cannula may be removed, then the tool (100, 200) may be turned around, and the remaining wound visualized and sutured.

In another example, it is useful to have a cannula tool and a visualization tool separate from one another. In a situation where a cannula becomes dislodged from a patient's eye during a procedure, it may be useful to be able to visualize the wound where the cannula became dislodged, and also to re-insert the cannula with a cannula tool as described in embodiments above, for example the tool 200 from FIG. 2.

Because both visualization and holding of the cannula are desired, in such a situation, it is useful to have both tools separate.

Figure 6:
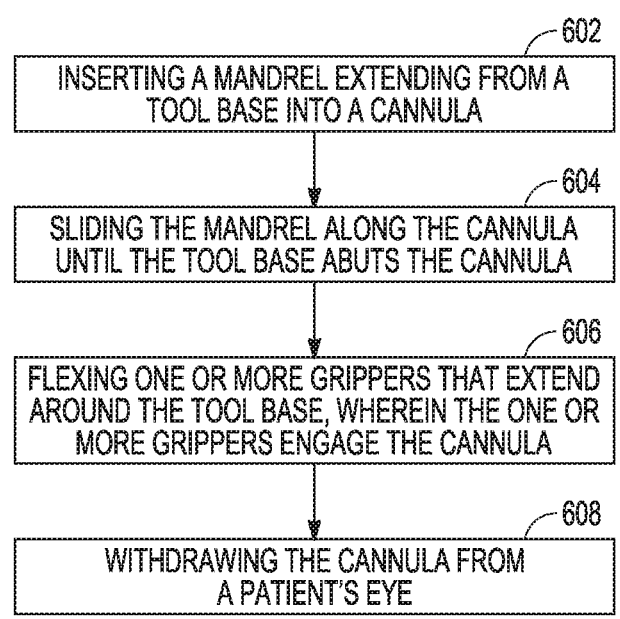
FIG. 6 shows an example method of using a cannula tool according to an embodiment of the invention.

FIG. 6 shows an example method of removing a cannula according to an example embodiment. In operation 602, a mandrel extending from a tool base is inserted into a cannula. In operation 604, the mandrel is passed along the cannula until the tool base abuts the cannula. In operation 606, one or more grippers that extend around the tool base are flexed to engage the cannula, and in operation 608, the cannula is withdrawn from the patient's eye.

To better illustrate the method and apparatuses disclosed herein, a non-limiting list of embodiments is provided here:

Example 1 includes an ophthalmic tool. The ophthalmic tool includes a handle, including a tool base sized to accept a cannula, a guide mandrel extending from the tool base, and at least one gripper extending around the tool base from the handle.

Example 2 includes the ophthalmic tool of example 1, wherein the at least one gripper includes a hooked end adapted to engage a ridge on a cannula when in use.

Example 3 includes the ophthalmic tool of any one of examples 1-2, wherein the tool base is substantially cylindrical with a base diameter that matches a cannula diameter.

Example 4 includes the ophthalmic tool of any one of examples 1-3, wherein the at least one gripper is integrally molded with the handle and are formed from a flexible material.

Example 5 includes the ophthalmic tool of any one of examples 1-4, wherein the at least one gripper includes two opposed grippers.

Example 6 includes the ophthalmic tool of any one of examples 1-5, further including a substantially transparent portion to place in contact with an eye near an ophthalmic wound.

Example 7 includes the ophthalmic tool of any one of examples 1-6, wherein the substantially transparent portion further includes a suture clearance cutaway to facilitate insertion of a suture while the substantially transparent portion is in contact with the eye.

Example 8 includes the ophthalmic tool of any one of examples 1-7, further including one or more frictional protrusions on one side of the substantially transparent portion.

Example 9 includes the ophthalmic tool of any one of examples 1-8, wherein the frictional protrusions include a number of teeth.

Example 10 includes the ophthalmic tool of any one of examples 1-9, wherein the transparent portion is hourglass shaped.

Example 11 includes the ophthalmic tool of any one of examples 1-10, wherein the transparent portion is glass.

Example 12 includes the ophthalmic tool of any one of examples 1-10, wherein the transparent portion is plastic.

Example 13 includes a method of removing a cannula, including inserting a mandrel extending from a tool base into a cannula, sliding the mandrel along the cannula until the tool base abuts the cannula, flexing one or more grippers that extend around the tool base, wherein the one or more grippers engage the cannula, and withdrawing the cannula from a patient's eye.

Example 14 includes the method of example 13, wherein flexing one or more grippers includes flexing two grippers that extend around the tool base, wherein the two grippers engage a ridge on the cannula.

Example 15 includes the method of any one of examples 13-14, wherein flexing one or more grippers includes flexing a single gripper against the mandrel to engage the cannula.

These and other examples and features of the present electronic device, and related methods will be set forth in part in the above detailed description. This overview is intended to provide non-limiting examples of the present subject matter—it is not intended to provide an exclusive or exhaustive explanation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An ophthalmic tool, comprising:
    a cannula, having a tube, and a cannula base coupled to the tube, wherein the cannula base is wider than the tube;
    a rigid handle, including a tool base sized to accept the cannula base;
    a guide mandrel extending to a permanently fixed location from the tool base; and
    at least one gripper extending around the tool base from the handle to a location past an end of the tool base, and configured to align with a side surface of the cannula base when the cannula base is pressed against the tool base.

2. The ophthalmic tool of claim 1, wherein the at least one gripper includes a hooked end adapted to engage a ridge on the cannula base when in use.

3. The ophthalmic tool of claim 1, wherein the tool base is substantially cylindrical with a base diameter that matches a cannula base diameter.

4. The ophthalmic tool of claim 1, wherein the at least one gripper is integrally molded with the handle and are formed from a flexible material.

5. The ophthalmic tool of claim 1, wherein the at least one gripper includes two opposed grippers.

6. The ophthalmic tool of claim 1, further including a substantially transparent portion coupled to the handle of the ophthalmic tool to place in contact with an eye near an ophthalmic wound.

7. The ophthalmic tool of claim 6, wherein the substantially transparent portion further includes a suture clearance cutaway to facilitate insertion of a suture while the substantially transparent portion is in contact with the eye.

8. The ophthalmic tool of claim 7, further including one or more frictional protrusions on one side of the substantially transparent portion.

9. The ophthalmic tool of claim 8, wherein the frictional protrusions include a number of teeth.

10. The ophthalmic tool of claim 7, wherein the transparent portion is hourglass shaped.

11. The ophthalmic tool of claim 6, wherein the transparent portion is glass.

12. The ophthalmic tool of claim 6, wherein the transparent portion is plastic.

13. A method of removing a cannula, comprising:
    inserting a mandrel extending from a tool base of a rigid handle into a cannula;
    sliding the mandrel along the cannula until the tool base abuts the cannula;
    flexing one or more grippers that extend around the tool base to a location past an end of the tool base, wherein the one or more grippers engage a side surface of the cannula while the cannula remains over the mandrel; and
    withdrawing the cannula from a patient's eye while the cannula remains over the mandrel.

14. The method of claim 13, wherein flexing one or more grippers includes flexing two grippers that extend around the tool base, wherein the two grippers engage a ridge on the cannula.

15. The method of claim 13, wherein flexing one or more grippers includes flexing a single gripper against the mandrel to engage the cannula.

* * * * *